United States Patent [19]

Madzsar

[11] Patent Number: 5,187,542
[45] Date of Patent: Feb. 16, 1993

[54] SPECTROSCOPIC WEAR DETECTOR

[75] Inventor: George C. Madzsar, North Olmsted, Ohio

[73] Assignee: The United States of America as represented by the Administrator of the National Aeronautics and Space Administration, Washington, D.C.

[21] Appl. No.: 722,446

[22] Filed: Jun. 27, 1991

[51] Int. Cl.$^5$ .................. G01J 3/00; G01N 21/00; G01N 17/00
[52] U.S. Cl. ........................ 356/300; 73/86; 60/223; 356/311; 356/36
[58] Field of Search ............ 356/300, 311, 72, 36; 73/86, 7; 60/271, 223; 239/71, 265.11; 250/302–303

[56] References Cited

U.S. PATENT DOCUMENTS

| | | | |
|---|---|---|---|
| 3,712,736 | 1/1973 | Boncoeur et al. | 356/300 |
| 3,735,591 | 5/1973 | Burkhart | 60/202 |
| 3,745,816 | 7/1973 | Erickson et al. | 356/72 |
| 4,120,196 | 10/1978 | Hamilton et al. | 73/104 |
| 4,514,797 | 4/1985 | Begin | 364/148 |
| 4,620,185 | 10/1986 | Plahmer | 340/682 |
| 4,774,150 | 9/1988 | Amano et al. | 428/690 |

OTHER PUBLICATIONS

Monika Auweter-Kurtz et al.; "Cathode Phenomena in Plasma Thrusters"; Jul. 18-20, 1990; AIAA 90-2662.
Kurtz et al.; "Mechanisms of Hot Cathode Erosion in Plasma Thrusters"; Jul. 18-20, 1990; AIAA 90-2673.

*Primary Examiner*—F. L. Evans
*Assistant Examiner*—K. P. Hantis
*Attorney, Agent, or Firm*—Gene E. Shook; Guy M. Miller; James A. Mackin

[57] ABSTRACT

The elemental composition of a material exposed to hot gasses and subjected to wear is determined. Atoms of an elemental species not appearing in this material are implanted in a surface at a depth based on the maximum allowable wear. The exhaust gasses are spectroscopically monitored to determine the exposure of these atoms when the maximum allowable wear is reached.

19 Claims, 3 Drawing Sheets

SPECTROSCOPIC WEAR DETECTOR

ORIGIN OF THE INVENTION

The invention described herein was made by an employee of the U.S. Government and may be manufactured and used by or for the Government of the United States for governmental purposes without the payment of any royalties thereon or therefor. Technical Field This invention is concerned with the monitoring and measurement of component wear using a non-intrusive and non-contact technique. The invention is based on the implantation of a substance into the component and then monitoring for that substance spectroscopically.

Hot cathode erosion in a plasma thruster is a problem that is being studied. A discussion of this phenomena can be found in AIAA paper Nos. 90-2662 and 90-2673 dated Jul. 18–20, 1990. The need for a reliable process for monitoring the erosion of the cathode in an MPD thruster is apparent from these publications.

Prior art wear monitoring techniques include physical measurement of the component with a micrometer to determine the amount of material lost. Another method measures the amount of material lost using isotopic wear detection which involves irradiating the component with radioactive isotopes. The amount of irradiation within the component is a function of depth. Near the surface the concentration of radioactive isotopes is greater than farther in the component. As the component wears, the isotopes also wear off. By measuring the residual radioactivity, the amount of material lost can be determined.

A number of disadvantages are encountered in using the prior art techniques. More particularly, measuring the wear induced dimensional changes using micrometers requires component disassembly which may be difficult and time-consuming. Isotope wear detection requires the use of radioactive isotopes which may be harmful to humans. Also, the use of radioactive isotopes requires that the half-life of the isotope be included into the wear equation. If the irradiated component is stored on a shelf for an extended period of time, the radioactivity may be sufficiently diminished, so that it cannot be measured.

It is, therefore, an object of the present invention to provide a procedure for the monitoring and measurement of component wear which does not require component disassembly.

Another object of the invention is to provide a non-intrusive and non-contact wear monitoring apparatus which does not utilize radioactive isotopes.

BACKGROUND ART

U.S. Pat. No. 3,712,736 to Boncoeur et al is concerned with testing welded work pieces by optical spectroscopy wherein a wire or film of a tracer element diffuses within a work piece when it is in a liquid state, and the presence of the tracer in plasma above the weld zone is continuously detected by spectroscopy.

U.S. Pat. No. 4,120,196 to Hamilton et al discloses a sensing device which monitors the distance to a selected wearing cutting surface of a tool and the distance to a selected non-wearing surface of the tool. U.S. Pat. No. 4,514,797 to Begin is likewise concerned with a worn tool detector system in which input signals from a sensor in the form of an analogue waveform exhibiting periodic impulses exceeding the average amplitude thereof are analyzed as the tool wears.

U.S. Pat. No. 4,620,185 to Plahmer describes a machine condition diagnostic system wherein machine components are labelled with wear indicator materials. The lubricant is examined and the presence of a particular indicator in abnormal amounts directs attention to a precise location in need of repair or replacement.

U.S. Pat. No. 4,774,150 to Amano et al provides a thermal barrier coating which allows nondestructive testing to determine whether the coating has a thickness sufficient for thermal barrier effect.

DISCLOSURE OF THE INVENTION

The objects of the invention are achieved by the implantation of a substance into a component and monitoring exhaust gasses for that substance spectroscopically to determine wear. In combustion engines the emission wavelength of the implanted species is monitored subsequent to thermal excitation in areas of wear.

BRIEF DESCRIPTION OF THE DRAWINGS

The aforementioned objects and advantages of the invention will be more clearly understood with reference to the drawings in which like numerals are used throughout to identify like parts.

BEST MODE FOR CARRYING OUT THE INVENTION

According to the present invention the elemental composition of the structure to be monitored for wear is determined. In the case of pure species such as gold, aluminum, iron, the composition is obvious. In the case of alloys, polymers, composites, or ceramics, the composition can be determined from published materials tables.

When all the elemental species appearing in the component are known, an elemental species, alloy, or material not appearing in the structure is selected. This selection is based on the following factors: 1) the species not normally appearing in the component, 2) the species being compatible with the materials of the structure, 3) and the species having a reasonably high transition probability and radiant power at a given wavelength. The wavelengths and transition probabilities are obtained from published literature. The radiant power can be calculated.

The selected species is implanted into the structure to a predetermined depth. This depth is based on the maximum allowable wear of the component. As the component wears, the implanted species eventually surfaces, and is released.

If the released implanted species is in a hot area of a combustion engine, its atoms are thermally excited and emit photons at a wavelength that is characteristic of the implanted species. By monitoring the exhaust gasses with emission spectroscopy equipment, the released atoms can be identified. Because the species was placed at a known depth, its observation in the exhaust gasses indicates the structure has worn down to the predetermined level.

Figure 1:
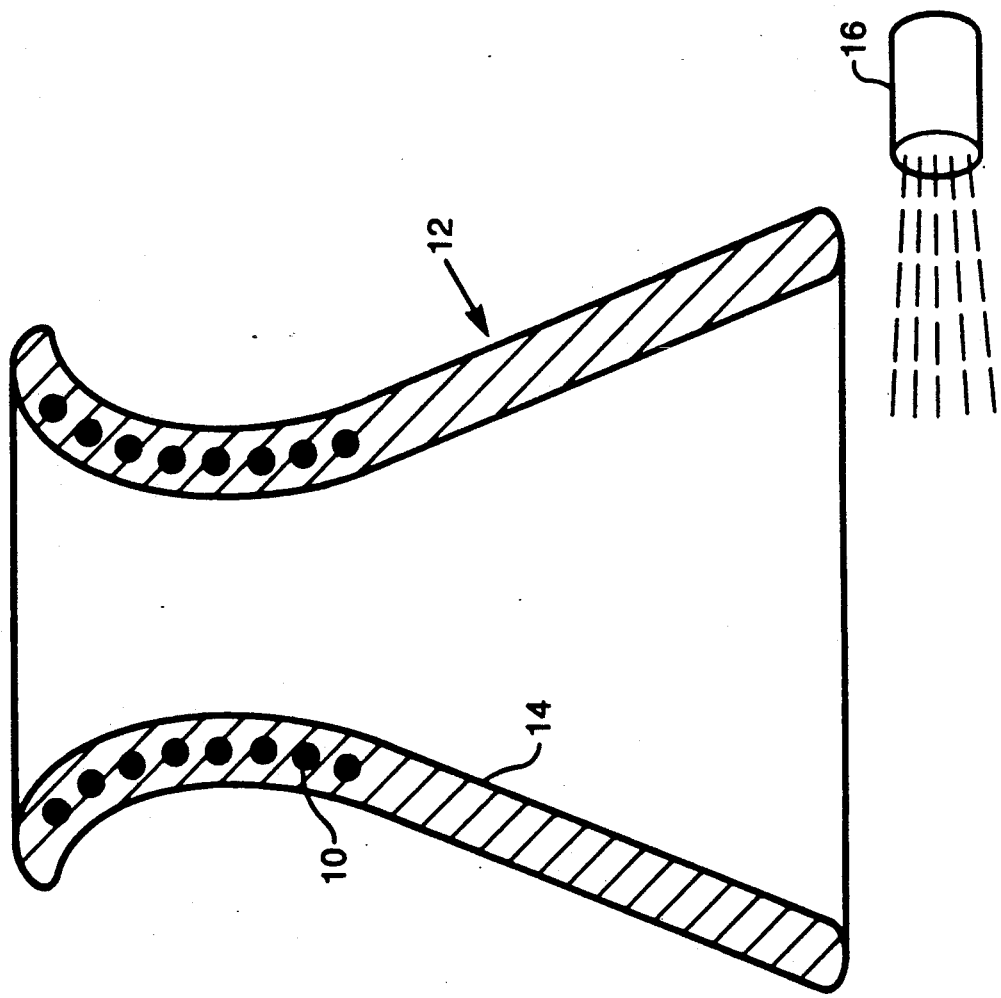
FIG. 1 is a section view of a hot nozzle showing atom implantation at a depth corresponding to the maximum allowable wear of the throat.
Figure 2:
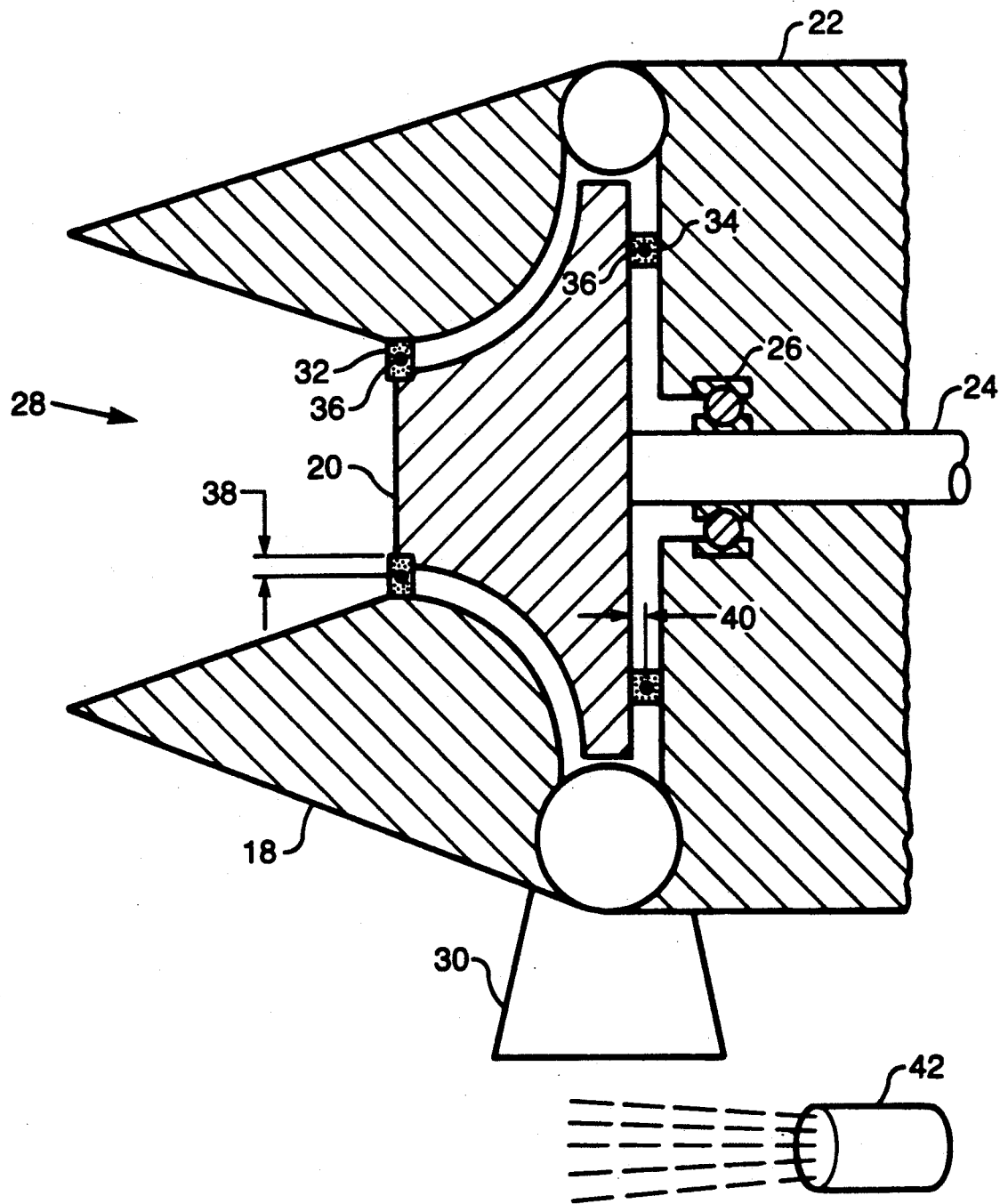
FIG. 2 is a section view of a turbopump showing atom implantation at a depth corresponding to the maximum allowable wear of the thrust pad and seal.

Referring now to the drawings there is shown in FIGS. 1 and 2 several embodiments of atom implantation in hot areas for wear detection. In FIG. 1 atoms 10 of a species that is thermally excited are implanted in the wall of a nozzle 12 a distance from the inner surface 14 that corresponds to the maximum allowable wear.

Exhaust gasses passing through the nozzle throat where the atoms 10 are implanted are monitored with emission spectroscopy equipment 16. As the nozzle throat wears, the atoms 10 of the thermally excitable species surface and are worn off into the exhaust gasses. These released atoms are identified by the equipment 16, and it is apparent that the maximum allowable wear has been reached.

FIG. 2 shows a turbopump 18 which comprises an impeller 20 which turns in a housing 22. The impeller 20 is mounted on a shaft 24 carried by a bearing 26. Hot gasses entering an inlet 28 in the housing 22 drive the impeller 20 which rotates the shaft 24. The spent gasses leave the housing 22 through an outlet 30.

A seal 32 in the inlet 28 is mounted in the space between the impeller 20 and the housing 22. A thrust pad 34 encircles the shaft 24 in the space between the rear surface of the impeller 20 and the housing 22.

According to the invention atoms 36 of a thermally excitable species are implanted in the seal 32 a distance 38 from the impeller 20 that corresponds to the maximum allowable wear. Likewise atoms 36 of the thermally excitable species are implanted in the thrust pad 34 a distance 40 from the back side of the impeller 20 which corresponds to the maximum allowable wear.

Emission spectroscopy equipment 42 monitors the hot gasses passing through the impeller 20 to identify released atoms. When maximum allowable wear in either the seal 32 or the thrust pad 34 is reached, atoms 36 will be released. This release is monitored by the equipment 42.

In order to illustrate the beneficial technical effect of the invention, tantalum was used to monitor wear of the surface of a tungsten cathode in a magnetoplasmadynamic, MPD, thruster of the type described in AIAA papers 90-2662 and 90-2675 dated Jul. 18-20, 1990. The operation of such a thruster is discussed further in U.S. Pat. No. 3,735,591 to Burkhart. The structure and operation of the MPD thruster form no part of the present invention.

Figure 3:
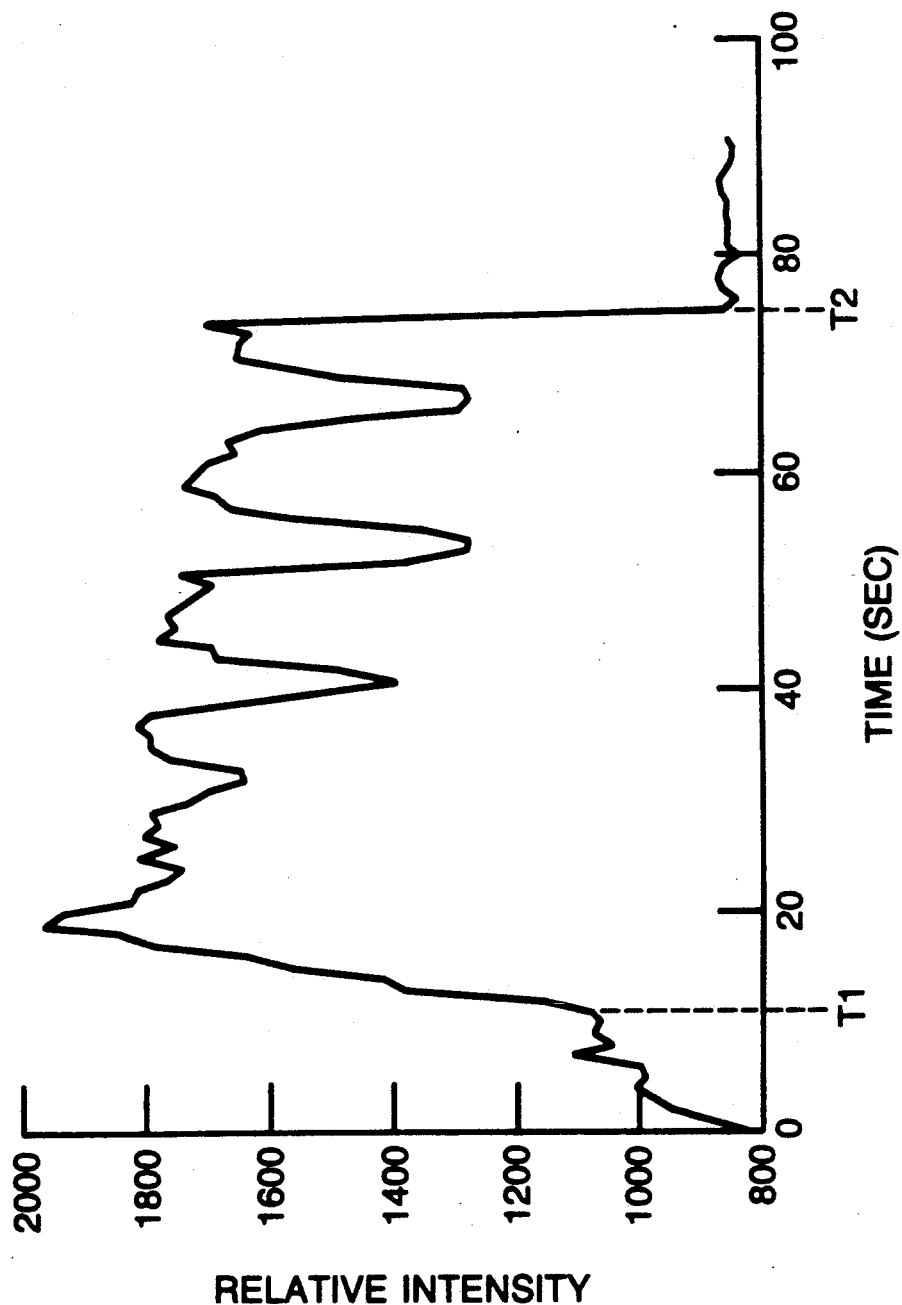
FIG. 3 is a graph showing the relative intensity of a tantalum spectral line plotted against time.

The intensity of a tantalum spectral line recorded from an MPD thruster is shown in FIG. 3. The MPD thruster utilized a tungsten cathode that was surrounded by a copper anode. This cathode typically experiences material erosion as stated in the aforementioned AIAA papers.

Tantalum was implanted under the surface of the tungsten cathode at a depth of ten (10) microns. The thruster was started and ran for a time sufficient to enable the cathode to erode thereby exposing the tantalum which then eroded away.

The graph shown in FIG. 3 shows the relative intensity of a tantalum spectral line at 362.62 nanometers recorded from the MPD thruster. T1 corresponds to the time when ten microns of tungsten has eroded thereby exposing the tantalum.

T2 corresponds to the time when substantially all of the tantalum has eroded away. The irregular intensity of the tantalum line between T1 and T2 is caused by uneven erosion of the tantalum.

This wear monitoring can be used in a relatively cool area using absorption rather than emission spectroscopy. By illuminating the exhaust gasses with light of a wavelength which is absorbed by released implanted atoms, the released implant absorbs the light. By measuring the decrease in light caused by absorption, the presence of the released implant can be detected.

The species can be implanted into a component by numerous techniques. Implanting can be accomplished by accelerating the atoms of the implant in a particle accelerator, and allowing the atoms to impact the component. The depth of penetration is a function of the energy gained by the atoms in the accelerator. An alternate approach would be to sputter the implant species into the structure, and then coat this sputtered layer with the same material as the component is fabricated from, resulting in an implanted layer under the surface of the structure. Chemical vapor deposition could also be used instead of sputtering.

While several preferred embodiments of the invention have been shown and described, it will be appreciated that various modifications can be made to the invention without departing from the spirit thereof or the scope of the subjoined claims. By way of example, while emission and absorption spectroscopy have been used to monitor the released atoms, it is contemplated that other spectroscopic techniques can be utilized.

We claim:

1. A nonintrusive and noncontact method of monitoring and measuring component wear resulting from material being eroded away in an apparatus emitting exhaust gasses to determine when said wear reaches a maximum allowable depth comprising determining the elemental composition of said material from which said component is formed, selecting an elemental species not appearing in said component, implanting atoms of said selected elemental species in a surface of said component which is subject to wear at said depth of maximum allowable wear, and spectroscopically monitoring said exhaust gases to detect the exposure of said atoms of said selected elemental species so that said maximum allowable wear has not been reached when no atoms of said selected elemental species are detected and said maximum allowable wear has been reached when said atoms are detected.

2. A method as claimed in claim 1 wherein the exhaust gasses are monitored with emission spectroscopy equipment to detect photons at a wavelength that is characteristic of the implanted atoms.

3. A method as claimed in claim 2 wherein atoms of the selected species are implanted in the wall of a nozzle.

4. A method as claimed in claim 2 wherein atoms of the selected species are implanted in the thrust pad and seal of a turbopump.

5. A method as claimed in claim 2 wherein atoms of the selected species are implanted in the cathode of a plasma thruster.

6. A method as claimed in claim 5 wherein tantalum atoms are implanted in a tungsten cathode.

7. A method as claimed in claim 1 wherein the exhaust gasses are monitored with absorption spectroscopy equipment.

8. A method as claimed in claim 7 wherein the exhaust gasses are illuminated with light of a wavelength which is absorbed by released implanted atoms.

9. A method as claimed in claim 8 wherein the decrease in light caused by absorption is measured.

10. In a method of monitoring wear of a component resulting from material being eroded away while in contact with exhaust gases to determine when said wear reaches a maximum allowable depth by detecting the presence of a selected elemental species not in the elemental composition of said component as said elemental species is released, the improvement comprising implanting atoms of said selected elemental species in a surface of said compound exposed to said exhaust gases at said maximum allowable depth, and sensing the presence of said selected elemental species in said exhaust gases only when said maximum allowable wear is reached whereby no elemental species is sensed when said wear has not reached said maximum allowable depth.

11. A method as claimed in claim 10 wherein the exhaust gasses are monitored with emission spectroscopy equipment to detect photons at a wavelength that is characteristic of the implanted atoms.

12. A method as claimed in claim 11 wherein atoms of the selected species are implanted in the wall of a nozzle.

13. A method as claimed in claim 11 wherein atoms of the selected species are implanted in the thrust pad and seal of a turbopump.

14. A method as claimed in claim 11 wherein atoms of the selected species are implanted in the cathode of a plasma thruster.

15. A method as claimed in claim 14 wherein tantalum atoms are implanted in a tungsten cathode.

16. A method as claimed in claim 15 wherein tantalum atoms are implanted in a tungsten cathode at a depth of ten microns.

17. A method as claimed in claim 10 wherein exhaust gasses are monitored with absorption spectroscopy equipment.

18. A method as claimed in claim 17 wherein the exhaust gasses are illuminated with a light of a wavelength which is absorbed by released implanted atoms.

19. A method as claimed in claim 18 wherein the decrease in light caused by absorption is measured.

* * * * *